United States Patent
Skinner

(10) Patent No.: US 9,546,949 B2
(45) Date of Patent: Jan. 17, 2017

(54) PARALLEL OPTICAL THIN FILM MEASUREMENT SYSTEM FOR ANALYZING MULTIANALYTES

(71) Applicant: Halliburton Energy Services, Inc., Houston, TX (US)

(72) Inventor: Neal G. Skinner, Lewisville, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/408,725

(22) PCT Filed: Dec. 20, 2013

(86) PCT No.: PCT/US2013/077017
§ 371 (c)(1),
(2) Date: Dec. 17, 2014

(87) PCT Pub. No.: WO2015/094351
PCT Pub. Date: Jun. 25, 2015

(65) Prior Publication Data
US 2015/0346087 A1    Dec. 3, 2015

(51) Int. Cl.
*G01N 21/55*    (2014.01)
*G01N 21/31*    (2006.01)
(Continued)

(52) U.S. Cl.
CPC ............ *G01N 21/31* (2013.01); *G01J 3/00* (2013.01); *G01J 3/2803* (2013.01); *G01J 3/32* (2013.01);
(Continued)

(58) Field of Classification Search
CPC ........ G01N 21/00; G01N 21/25; G01N 21/17; G01N 21/27; G01N 21/62; G01N 21/63; G01N 2021/635
See application file for complete search history.

(56) References Cited

U.S. PATENT DOCUMENTS 6,529,276 B1 * 3/2003 Myrick ................. G01J 3/02
356/310
2013/0031964 A1    2/2013 Tunheim et al.
(Continued)

FOREIGN PATENT DOCUMENTS

JP    2012127900    7/2012
KR    2013-0131412 A    12/2013
WO    2015094351 A1    6/2015

OTHER PUBLICATIONS

International Search Report and Written Opinion for PCT/US2013/077017 dated Sep. 26, 2014.

*Primary Examiner* — Tony Ko
(74) *Attorney, Agent, or Firm* — McDermott Will & Emery LLP; Benjamin Fite

(57) ABSTRACT

Optical computing devices including a light source that emits electromagnetic radiation into an optical train extending from the light source to a detector, a substance arranged in the optical train and configured to optically interact with the electromagnetic radiation and produce sample interacted radiation, a processor array arranged in the optical train and including a plurality of ICE arranged on a substrate and configured to optically interact with the electromagnetic radiation. The detector receives modified electromagnetic radiation generated through optical interaction of the electromagnetic radiation with the substance and the processor array. A weighting device is coupled to one or more of the ICE to optically apply a weighting factor to the modified electromagnetic radiation prior to being received by the detector, wherein the detector generates an output signal indicative of a characteristic of the substance based on beams of modified electromagnetic radiation.

22 Claims, 9 Drawing Sheets

(51) Int. Cl.
    *G01N 21/27*     (2006.01)
    *G01J 3/00*     (2006.01)
    *G01N 21/25*     (2006.01)
    *G01J 3/28*     (2006.01)
    *G01J 3/32*     (2006.01)
    G01N 21/552     (2014.01)
    G01J 3/12     (2006.01)

(52) U.S. Cl.
    CPC ............ *G01N 21/255* (2013.01); *G01N 21/27* (2013.01); *G01N 21/314* (2013.01); *G01J 2003/1226* (2013.01); *G01N 21/552* (2013.01); *G01N 2201/062* (2013.01); *G01N 2201/06113* (2013.01); *G01N 2201/12* (2013.01); *G01N 2201/1296* (2013.01)

(56) References Cited

U.S. PATENT DOCUMENTS

2013/0284894 A1    10/2013    Freese et al.
2013/0287061 A1    10/2013    Freese et al.

\* cited by examiner

PARALLEL OPTICAL THIN FILM MEASUREMENT SYSTEM FOR ANALYZING MULTIANALYTES

BACKGROUND

The present disclosure relates to optical computing devices and, more particularly, to optical computing devices that employ improved optical processing element configurations used to make parallel measurements of sample substances.

Optical computing devices, also commonly referred to as "opticoanalytical devices," can be used to analyze and monitor a sample substance in real time. Such optical computing devices will often employ a light source that emits electromagnetic radiation that reflects from or is transmitted through the sample and optically interacts with an optical processing element to determine quantitative and/or qualitative values of one or more physical or chemical properties of the substance. The optical processing element may be, for example, an integrated computational element (ICE). An ICE can be an optical thin film interference device, also known as a multivariate optical element (MOE), which can be designed to operate over a continuum of wavelengths in the electromagnetic spectrum from the UV to mid-infrared (MIR) ranges, or any sub-set of that region. Electromagnetic radiation that optically interacts with the sample substance is changed and processed by the ICE so as to be measured by a detector, such that an output of the detector can be correlated to the physical or chemical property of the substance being analyzed.

In some configurations, multiple ICE cores may be used in an optical computing device to detect a particular characteristic or analyte of interest. The optical responses from each ICE core are sequentially measured by a single detector, and an associated signal processor computationally combines the several responses using coded software such that a linear combination of the responses is obtained and correlated to the analyte of interest. Computationally combining the responses can include determining a weighted average of the various responses in order to obtain the best measurement of the analyte of interest. Since these measurements and computations are performed sequentially, this process takes time.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
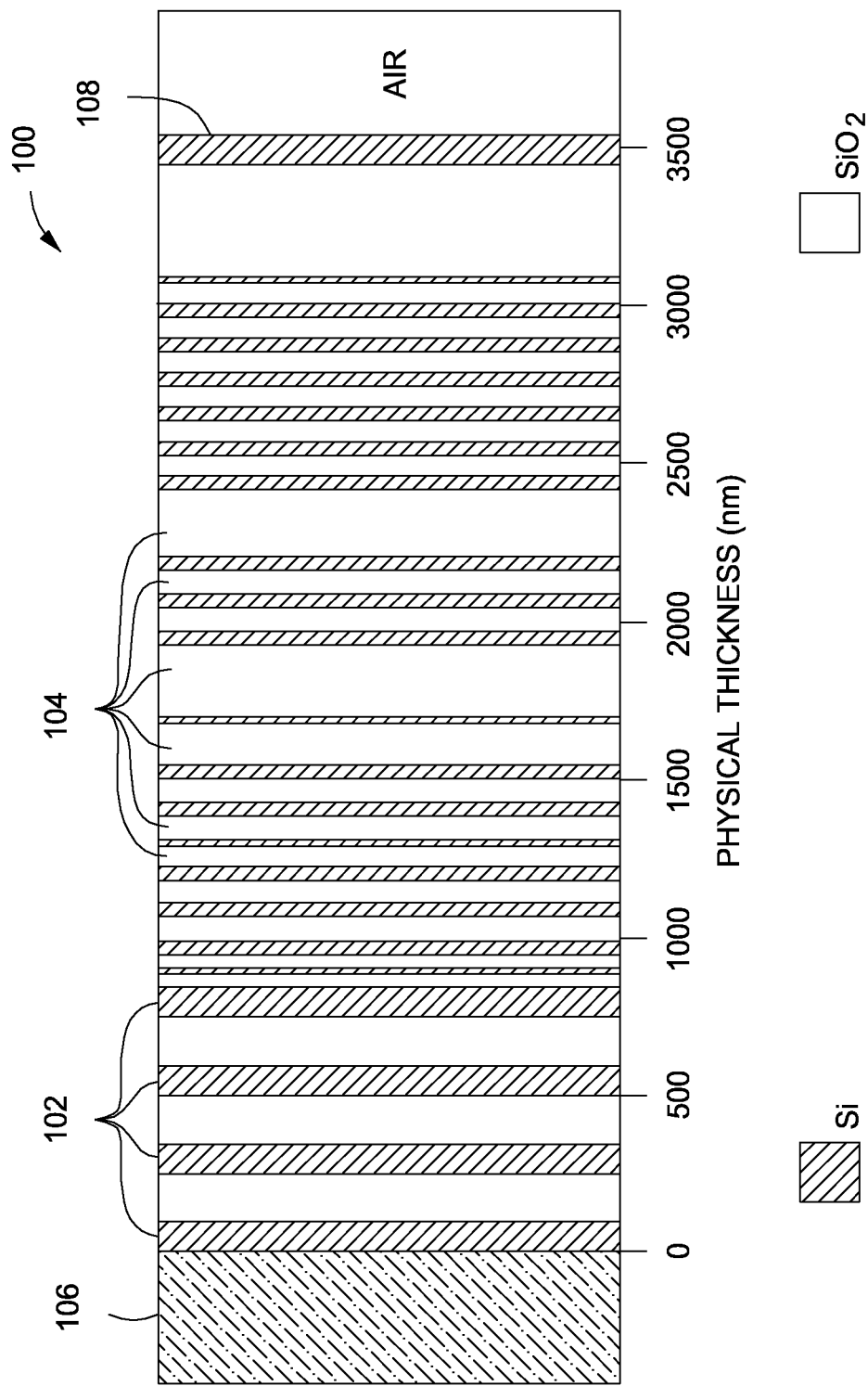
FIG. 1 illustrates an exemplary integrated computation element, according to one or more embodiments.

The present disclosure relates to optical computing devices and, more particularly, to optical computing devices that employ improved optical processing element configurations used to make parallel measurements of sample substances.

The exemplary systems and methods described herein employ various configurations of optical computing devices, also commonly referred to as "opticoanalytical devices," for the real-time or near real-time monitoring of a sample substance. The optical computing devices optically apply weighting factors to derived response signals, as opposed to digitally applying the weighting factors using a signal processor and associated software applications. One disclosed optical computing device includes an array of thin film interference filters having various weighting factors applied directly thereto. The array provides a detector with a modified optical signal already having weighting factors applied thereto. Another disclosed optical computing device includes an array of integrated computational elements (ICE) and a dynamic array of weighting devices that are able to change the weighting factors applied to each ICE in real-time. As a result, an ICE array is able to detect and otherwise analyze multiple analytes by altering the weighting factors of the dynamic weighting array. Accordingly, what has previously been done in post-processing operations using software applications in the signal processor can now be done in real-time by dynamically modifying a weighting array.

The presently described optical computing devices may be suitable for use in the oil and gas industry since they provide a cost-effective, rugged, and accurate means of monitoring and detecting oil/gas-related substances, such as hydrocarbons, drilling fluids, or completion fluids. Those skilled in the art, however, will readily recognize that the presently described systems and methods may equally be advantageous and otherwise applicable to other fields of technology or industries including, but not limited to, the food industry, the paint industry, the mining industry, the agricultural industry, the medical and pharmaceutical industries, the automotive industry, the cosmetics industry, water treatment facilities, and any other field where it may be desired to monitor substances in real time.

As used herein, the term "characteristic" or "characteristic of interest" refers to a chemical, mechanical, or physical property of a substance or a sample of the substance. The characteristic of a substance may include a quantitative or qualitative value of one or more chemical constituents or compounds present therein or any physical property associated therewith. Such chemical constituents and compounds may be referred to herein as "analytes." Illustrative characteristics of a substance that can be detected with the optical computing devices described herein can include, for example, chemical composition (e.g., identity and concentration in total or of individual components), phase presence (e.g., gas, oil, water, etc.), impurity content, pH, alkalinity, viscosity, density, ionic strength, total dissolved solids, salt content (e.g., salinity), porosity, opacity, bacteria content, total hardness, transmittance, combinations thereof, state of matter (solid, liquid, gas, emulsion, mixtures thereof, etc.), and the like.

As used herein, the term "substance," or variations thereof, refers to at least a portion of matter or material of interest to be tested or otherwise evaluated using the optical computing devices described herein. The substance includes the characteristic of interest, as defined above. The substance may be any fluid capable of flowing, including particulate solids, liquids, gases (e.g., air, nitrogen, carbon dioxide, argon, helium, methane, ethane, butane, and other hydrocarbon gases, hydrogen sulfide, and combinations thereof), slurries, emulsions, powders, muds, glasses, mixtures, combinations thereof, and may include, but is not limited to, aqueous fluids (e.g., water, brines, etc.), non-aqueous fluids (e.g., organic compounds, hydrocarbons, oil, a refined component of oil, petrochemical products, and the like), acids, surfactants, biocides, bleaches, corrosion inhibitors, foamers and foaming agents, breakers, scavengers, stabilizers, clarifiers, detergents, treatment fluids, fracturing fluids, formation fluids, or any oilfield fluid, chemical, or substance commonly found in the oil and gas industry. In some cases, the substance may also refer to a solid material such as, but not limited to, rock formations, concrete, solid wellbore surfaces, pipes or flow lines, and solid surfaces of any wellbore tool or projectile (e.g., balls, darts, plugs, etc.).

As used herein, the term "fluid" refers to any substance that is capable of flowing, including particulate solids, liquids, gases, slurries, emulsions, powders, muds, mixtures, combinations thereof, and the like. In some embodiments, the fluid may be a drilling fluid or drilling mud, including water-based drilling fluids, oil-based drilling fluids, synthetic drilling fluids, and the like. In other embodiments, the fluid may be a completion fluid or clean-up fluid such as, but not limited to, fresh water, saltwater (e.g., water containing one or more salts dissolved therein), brine (e.g., saturated salt water, chloride salts, bromide salts, combinations thereof, etc.), seawater, a spacer fluid, base fluids, or other treatment fluids known in the art.

As used herein, the term "electromagnetic radiation" refers to radio waves, microwave radiation, terahertz, infrared and near-infrared radiation, visible light, ultraviolet light, X-ray radiation and gamma ray radiation.

As used herein, the term "optically interact" or variations thereof refers to the reflection, transmission, scattering, diffraction, or absorption of electromagnetic radiation either on, through, or from one or more processing elements (i.e., an optical interference device), a substance being analyzed by the processing elements, or a polarizer. Accordingly, optically interacted light refers to electromagnetic radiation that has been reflected, transmitted, scattered, diffracted, or absorbed by, emitted, or re-radiated, for example, using a processing element, but may also apply to optical interaction with a substance or a polarizer.

As indicated above, optical computing devices can employ processing elements in the form of optical interference devices. One optical interference device that may be used is an integrated computational element (ICE), referred to herein as an "ICE core". In operation, an ICE core is capable of distinguishing electromagnetic radiation related to a characteristic of interest of a substance from electromagnetic radiation related to other components of the substance.

Referring to FIG. 1, illustrated is an exemplary ICE core 100 that may be used in the systems described herein. As illustrated, the ICE core 100 may include a plurality of alternating thin film layers 102 and 104, such as silicon (Si) and $SiO_2$ (quartz), respectively. In general, these layers 102, 104 consist of materials whose index of refraction is high and low, respectively. Other examples of materials might include niobia and niobium, germanium and germania, MgF, SiO, and other high and low index materials known in the art. The layers 102, 104 may be strategically deposited on an optical substrate 106. In some embodiments, the optical substrate 106 is BK-7 optical glass. In other embodiments, the optical substrate 106 may be another type of optical substrate, such as another optical glass, silica, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the optical substrate 106 in FIG. 1), the ICE core 100 may include a layer 108 that is generally exposed to the environment of the device or installation, and may be able to detect a sample substance. The number of layers 102, 104 and the thickness of each layer 102, 104 are determined from the spectral attributes acquired from a spectroscopic analysis of a characteristic of the substance being analyzed using a conventional spectroscopic instrument. The spectrum of interest of a given characteristic typically includes any number of different wavelengths.

It should be understood that the ICE core 100 depicted in FIG. 1 does not in fact represent any particular ICE core configured to detect a specific characteristic of a given substance, but is provided for purposes of illustration only. Consequently, the number of layers 102, 104 and their relative thicknesses, as shown in FIG. 1, bear no correlation to any particular substance or characteristic thereof. Nor are the layers 102, 104 and their relative thicknesses necessarily drawn to scale, and therefore should not be considered limiting of the present disclosure.

In some embodiments, the material of each layer 102, 104 can be doped or two or more materials can be combined in a manner to achieve the desired optical characteristic. In addition to solids, the exemplary ICE core 100 may also contain liquids and/or gases, optionally in combination with solids, in order to produce a desired optical characteristic. In the case of gases and liquids, the ICE core 100 can contain a corresponding vessel (not shown), which houses the gases or liquids. Exemplary variations of the ICE core 100 may also include holographic optical elements, gratings, piezoelectric, light pipe, and/or acousto-optic elements, for example, that can create transmission, reflection, and/or absorptive properties of interest.

The multiple layers 102, 104 may exhibit different refractive indices. By properly selecting the materials of the layers 102, 104 and their relative thickness and spacing, the ICE core 100 may be configured to selectively transmit or reflect predetermined fractions of electromagnetic radiation at different wavelengths. Each wavelength is given a predetermined weighting or loading factor. The thickness and spacing of the layers 102, 104 may be determined using a variety of approximation methods from the spectrum of the characteristic or analyte of interest. These methods may include inverse Fourier transform (IFT) of the optical transmission spectrum and structuring the ICE core 100 as the physical representation of the IFT. The approximations convert the IFT into a structure based on known materials with constant refractive indices.

The weightings that the layers 102, 104 of the ICE core 100 apply at each wavelength may be set to the regression weightings described with respect to a known equation, data, or spectral signature. For instance, when electromagnetic radiation interacts with a substance, unique physical and chemical information about the substance is encoded in the electromagnetic radiation that is reflected from, transmitted through, or radiated from the substance. This information is often referred to as the spectral "fingerprint" of the substance. The ICE core 100 may be configured to perform the dot product of the received electromagnetic radiation and the wavelength dependent transmission function of the ICE core 100. The wavelength dependent transmission function of the ICE core 100 is dependent on the material refractive index of each layer, the number of layers 102, 104 and thickness of each layer 102, 104.

One type or variation of an ICE core 100 is a frequency selective surface (FSS) ICE core. The FSS ICE core is substantially similar to the ICE core 100 described above, but instead of having a stack of dielectric thin film layers 102, 104, an FSS ICE core includes a single, periodically-patterned metallic thin film layer. Upon optically interacting with electromagnetic radiation, each FSS ICE core generates an optical processing function that is dependent on the shape of the FSS structure, the type of metal used for the thin film layer and the thickness of the metal layer.

Figure 2:
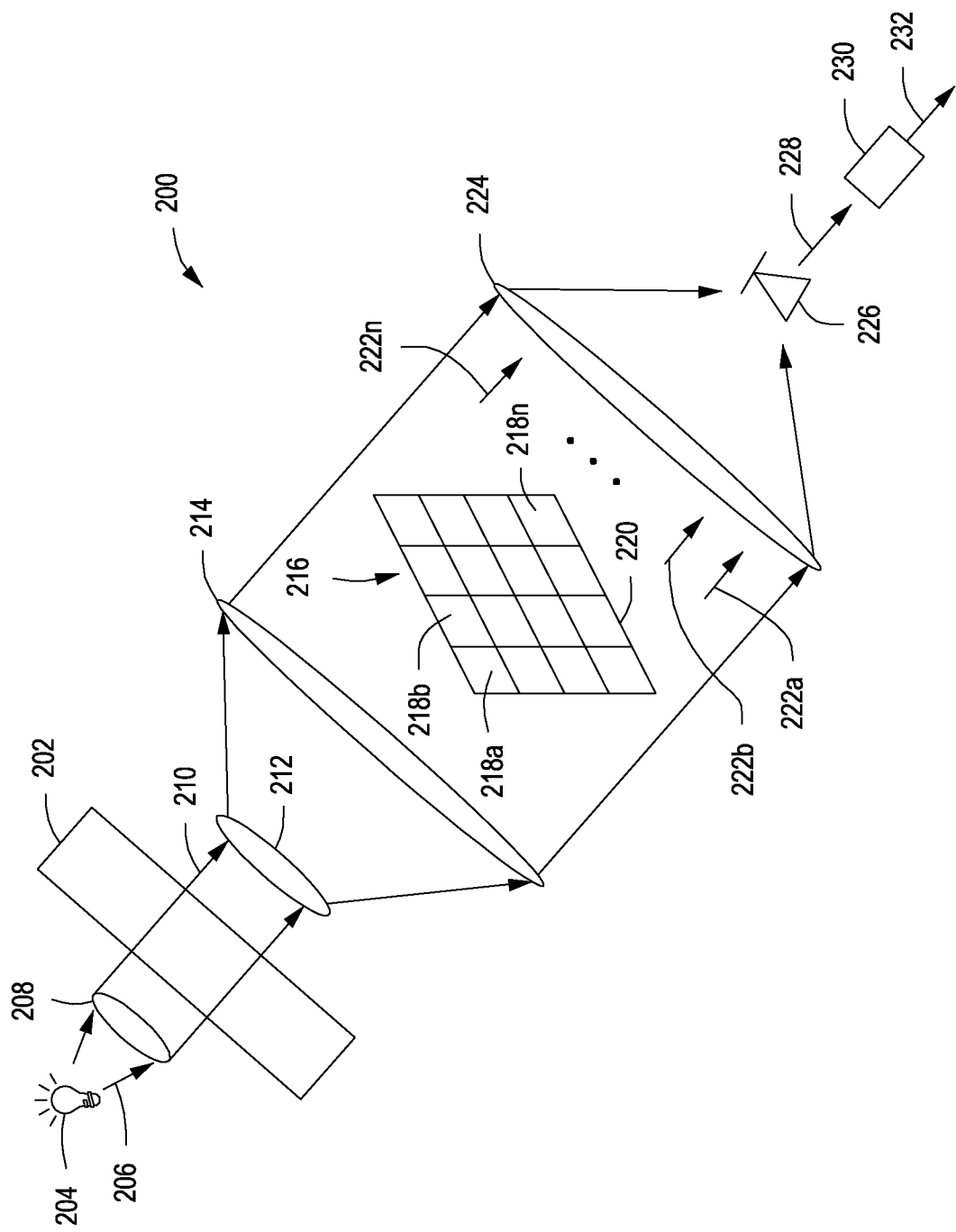
FIG. 2 illustrates an exemplary optical computing device for analyzing a substance, according to one or more embodiments.

Referring now to FIG. 2, illustrated is an exemplary optical computing device 200 (hereafter "device 200") that may be used in analyzing a substance 202, according to one or more embodiments. The device 200 may be configured to determine a characteristic of interest in the substance 202, such as the concentration of an analyte present therein. In some embodiments, the substance 202 may be contained in a fluid sampling chamber or the like. In other embodiments, the substance 202 may be a fluid flowing within a flow line, a pipeline, a wellbore, an annulus defined within a wellbore, or any flow lines or pipelines extending to/from a wellbore. In yet other embodiments, the substance 202 may be disposed within any other containment or storage vessel known to those skilled in the oil and gas industry. Accordingly, it is contemplated herein that the device 200 may be used in laboratory as well as field conditions or applications, without departing from the scope of the disclosure.

The device 200 includes a light source 204 configured to emit or otherwise generate electromagnetic radiation 206. The light source 204 may be, for example, a light bulb, a light emitting diode (LED), a laser, a blackbody, a photonic crystal, an X-Ray source, a supercontinuum source, combinations thereof, or the like. In some embodiments, a first collimator 208 may be configured to collect or otherwise receive the electromagnetic radiation 206 and direct a collimated beam of electromagnetic radiation 206 toward the substance 202. In other embodiments, the first collimator 208 may be omitted from the device 200 and the electromagnetic radiation 206 may instead be directed toward the substance 202 directly from the light source 204.

In the illustrated embodiment, the electromagnetic radiation 206 is transmitted through the substance 202 where it impinges upon and optically interacts with the substance 202, including any components or analytes present within the substance 202. As a result, sample interacted radiation 210 is generated by the substance 202 and conveyed further downstream within the optical train. Those skilled in the art will readily recognize that alternative variations of the device 200 may allow the sample interacted radiation 210 to be generated by being reflected, scattered, diffracted, absorbed, emitted, or re-radiated by and/or from the substance 202, without departing from the scope of the disclosure.

In at least one embodiment, the sample interacted radiation 210 is generated by an evanescent wave, which may be generated through attenuated total reflectance (ATR) sampling techniques known to those skilled in the art. More particularly, evanescent waves are formed when light waves or beams traveling in a medium (e.g., an ATR crystal or the like) undergo total internal reflection at the boundaries of the medium because they strike the boundaries at an angle greater than the "critical" angle. An evanescent wave is subsequently produced from the medium and directed toward a sample (i.e., the substance 202), and the interaction of the evanescent wave with the sample induces absorption and allows for spectroscopic interrogation of the sample.

In some embodiments, the sample interacted radiation 210 generated by interaction with the substance 202 may be directed to or otherwise received by an expander 212, also known as a "beam expander". The expander 212 may be any device capable of expanding the size of a beam of light, such as the sample interacted radiation 210. A second collimator 214 may be arranged within the optical train to receive and collimate the sample interacted radiation 210 from the expander 212. The second collimator 214 may be similar to the first collimator 208 discussed above and therefore configured to produce a substantially collimated or parallel beam of electromagnetic radiation.

The second collimator 214 may be configured to convey the sample interacted radiation 210 toward a processor array 216 arranged within the optical train. The processor array 216 may be configured to receive and optically interact with the sample interacted radiation 210. The processor array 216 may include several ICE cores 218 (shown as ICE cores 218a, 218b, . . . and 218n) strategically and individually arranged on a substrate 220. Each ICE core 218a-n may be an optical interference device similar to the ICE core 100 described above with reference to FIG. 1. In other embodiments, the ICE cores 218a-n may be any other type of optical interference device, such as an FSS ICE core described above, without departing from the scope of the disclosure.

The substrate 220 may be any optical substrate including, but not limited to, BK-7 optical glass, other types of optical glass, quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like. As depicted, the ICE cores 218a-n are separately and individually arranged on the substrate 220 in a square four row by four-column matrix. One of skill in the art, however, will readily appreciate that the ICE cores 218a-n may be arranged in any predetermined pattern or sequence, without departing from the scope of the disclosure. Moreover, the processor array 216 and associated substrate 220 does not necessarily have to be square, but could likewise be formed in any polygonal shape (e.g., rectangular, hexagonal, pentagonal, linear, etc.). In yet other embodiments, the processor array 216 and substrate 220 may be circular, oval, or ovoid in shape, without departing from the scope of the disclosure. Moreover, while a certain number of ICE cores 218a-n are depicted in FIG. 2 as being arranged on the substrate 220, those skilled in the art will readily recognize that more or less ICE cores 218a-n than those depicted may be employed in the device 200.

Each ICE core 218a-n arranged on the substrate 220 may be configured to detect a particular characteristic of the substance 202. In some embodiments, two or more of the ICE cores 218a-n may be configured to detect the same characteristic of interest. In other embodiments, however, each ICE core 218a-n may be configured to detect a different or distinct characteristic of interest of the substance 202.

Moreover, one or more of the ICE cores 218a-n has a weighting factor associated therewith and otherwise forms an integral part thereof. The weighting factor may be applied to the ICE cores 218a-n through the use of a weighting device, such as a neutral density filter, configured to reduce the intensity of the sample interacted radiation 210 by a predetermined or specific quantity. As a result, the corresponding ICE core 218a-n will transmit a certain normalized intensity of light ranging from 0 to 1, where 0 is a minimum intensity of light passing through the ICE core 218a-n, and 1 is the maximum intensity of light passing through the ICE core 218a-n.

In other embodiments, the weighting device may be an optical iris, a pinhole, an aperture, or the like arranged on or otherwise associated with one or more of the ICE cores 218a-n. Depending on the design and configuration of the weighting device, a particular static weighting factor is applied to the ICE cores 218a-n that alter the output signal of the corresponding ICE cores 218a-n to a particular or predetermined characteristic or analyte of interest.

In operation, the ICE cores 218a-n each receive and optically interact with the sample interacted radiation 210. Such optical interaction includes simultaneous interaction with the particular weighting factors applied to each corresponding ICE core 218a-n. Corresponding beams of modified electromagnetic radiation 222 (shown as modified electromagnetic radiation 222a, 222b, . . . and 222n) are generated from each respective ICE core 218a-n in the processor array 216. Each beam of modified electromagnetic radiation 222a-n is electromagnetic radiation that has optically interacted with its corresponding ICE core 218a-n (and any weighting factor applied thereto), whereby an approximation of the regression vector corresponding to the characteristic of the substance 202 associated with the respective ICE core 218a-n is obtained.

The modified electromagnetic radiation 222a-n may then be directed to an optical focusing element 224 arranged within the optical train. The optical focusing element 224 may be any type of optical element capable of focusing the modified electromagnetic radiation 222a-n toward a point. For example, the optical focusing element 224 may be similar to the expander 212, except used in reverse to reduce the size of a beam of light. The optical focusing element 224 focuses the beams of modified electromagnetic radiation 222a-n toward a detector 226 for integrating the several optical responses from the ICE cores 218a-n. The detector 226 may be any device capable of detecting electromagnetic radiation, and may be generally characterized as an optical transducer. In some embodiments, the detector 226 may be, but is not limited to, a thermal detector such as a thermopile or photoacoustic detector, a semiconductor detector, a piezoelectric detector, a charge coupled device (CCD) detector, a video or array detector, a split detector, a photon detector (such as a photomultiplier tube), photodiodes, combinations thereof, or the like, or other detectors known to those skilled in the art.

The detector 226 may be configured to produce an output signal 228 in real-time or near real-time in the form of a voltage (or current) that corresponds to the particular characteristic of interest in the substance 202. The voltage returned by the detector 226 is essentially the dot product of the optical interaction of the sample interacted radiation 210 with the respective ICE cores 218a-n as a function of the magnitude of the characteristic of interest of the substance 202, such as concentration. As such, the output signal 228 produced by the detector 226 and the concentration of the characteristic may be directly proportional. In other embodiments, however, the relationship may correspond to a polynomial function, an exponential function, a logarithmic function, and/or a combination thereof.

The output signal 228 may be conveyed to or otherwise received by a signal processor 230 communicably coupled to the detector 226. The signal processor 230 may be a computer including a processor and a machine-readable storage medium having instructions stored thereon, which, when executed by the processor, cause the device 200 to perform a number of operations, such as determining a characteristic of interest of the substance 202. For instance, the concentration of the characteristic detected with the device 200 can be fed into an algorithm operated by the signal processor 230. The algorithm can be part of an artificial neural network configured to use the concentration of the detected characteristic in order to evaluate the overall quality of the substance 202.

In real-time or near real-time, the signal processor 230 may be configured to provide a resulting output signal 232 corresponding to the characteristic of interest in the substance 202 as cooperatively measured by the several ICE cores 218a-n. Advantageously, since the weighting factors are already applied to the ICE cores 218a-n, the detector 226 automatically receives the weighted average of the modified electromagnetic radiation 222a-n and the output signal 228 generated therefrom is indicative of the same. As a result, the signal processor 230 is not required to digitally apply various weighting factors to the signals derived from each ICE core 218a-n and otherwise consider the weighting factors when computing and generating the resulting output signal 232. Rather, the weighting factors are optically applied to the resulting output signal 232 when the sample interacted radiation 210 optically interacted with the processor array 216 and its associated static weighting factors already applied thereto.

As further explanation, in prior optical computing devices, a characteristic of the substance 202 would be identified by sequentially combining the outputs of several ICE cores in the signal processor 230. The optical outputs from each ICE core would be measured sequentially and a linear combination of these outputs as generated by the signal processor 230 would be used to determine the particular characteristic of the substance 202. Mathematically, this can be done using the following equation:

$$\text{Output} = \sum_{i=1}^{n} W_i \int A_i(\lambda) I_i(\lambda) d\lambda \qquad \text{Equation (1)}$$

where $W_i$ is a weighting factor to be applied digitally in the signal processor 230, $A_i(\lambda)$ is the optical transmission function for each ICE core, $I_i(\lambda)$ is the transmission spectrum of light leaving the substance 202, and n is the number of ICE cores used in the model. In traditional computational methods, the individual dot products of the optical transmission function $A_i(\lambda)$ and the transmission spectrum $I_i(\lambda)$ are generally proportional to the concentration of the characteristic of interest, and predetermined weighting factors ($W_i$) are digitally applied to each output signal 228 in the signal processor 230 to obtain a single resulting output signal 232 corresponding to a single characteristic of interest. More particularly, the software used by the signal processor 230 takes the several output signals 228 from the detector 226 and adds them together along with the predetermined weighting factors for each output signal 228. Accordingly, the resulting output signal 232 provides a digital representation of the weighting factors as applied to the output signals 228.

According to the present disclosure, however, the weighting factors are applied optically to the optical responses for each ICE core 218a-n prior to reaching the detector 226, and thereby creating a new filter function ($F_i$). Defining the new filter function ($F_i$) as the weighting factor ($W_i$) multiplied by the optical transmission function for each ICE core ($A_i$), Equation (1) above can be rewritten as follows:

$$\text{Output} = \sum_{i=1}^{n} \int F_i(\lambda) I_i(\lambda) d\lambda \qquad \text{Equation (2)}$$

where the weighting factors $W_i$ and the optical transmission functions $A_i(\lambda)$ for each ICE core 218a-n are combined to obtain the new filter function $F_i(\lambda)$. As a result, the weighting factors are applied optically to the optical responses generated by each ICE core 218a-n, instead of digitally through software manipulation carried out in the signal processor 230. Accordingly, instead of being required to measure each ICE core 218a-n sequentially in time, and subsequently apply a weighting factor thereto digitally, the present disclosure provides a means to measure the optical responses of each ICE core 218a-n in view of a predetermined weighting factor simultaneously. Moreover, mathematically, the detector 226 sees the responses simultaneously, and not in time. Therefore, the signal measured by the detector 226 already includes all the weighting factors applied thereto, and the signal processor 230 is therefore not required to subsequently apply the weighting factors during computation.

As will be appreciated, this will result in faster sampling times when using multiple multivariate models, for example neural networks, associated with several ICE cores 218a-n. More particularly, when multivariate models are used to determine properties or characteristics of a substance 202 via multiple ICE cores 218a-n, only one optical measurement needs to be made since the measurements are now being made in parallel and not sequentially.

Those skilled in the art will readily appreciate that various configurations of the device 200 may be employed, without departing from the scope of the disclosure. For instance, while FIG. 2 depicts the processor array 216 as receiving the electromagnetic radiation as transmitted through the substance 202, the processor array 216 may equally be arranged at any point along the optical train of the device 200. For example, in one or more embodiments, the processor array 216 may be arranged within the optical train between the light source 204 and the substance 202 and equally obtain substantially the same results. Moreover, in other embodiments, the processor array 216 may generate the modified electromagnetic radiation 222 through reflection, instead of transmission therethrough.

In yet other embodiments, one or all of the first and second collimators 208, 214, the expander 212, and the optical focusing element 224 may be omitted from the device 200 or otherwise rearranged to accommodate the position of the processor array 216 in the optical train. For instance, in at least one embodiment, the expander 212 may be arranged prior to the substance 202 in the optical train such that the electromagnetic radiation 206 is expanded prior to transmission through or reflection from the substance 202.

In even further embodiments, one or more spatial filters (not shown) may be arranged at one or more locations throughout the optical train, such as prior to the processor array 216. Placing a spatial filter prior to the processor array 216 may result in a beam of light with a more uniform irradiance across the processor array 216. In other embodiments, a spatial filter may be in the form of a small hole or the like and located within the optical train between the light source 204 and the first collimator 208. Placing a spatial filter at that location may make the light source 204 appear more like a point source. Those skilled in the art of optics will readily appreciate the various alternative configurations that the device 200 may exhibit and otherwise incorporate, without departing from the scope of the disclosure.

Figure 3:
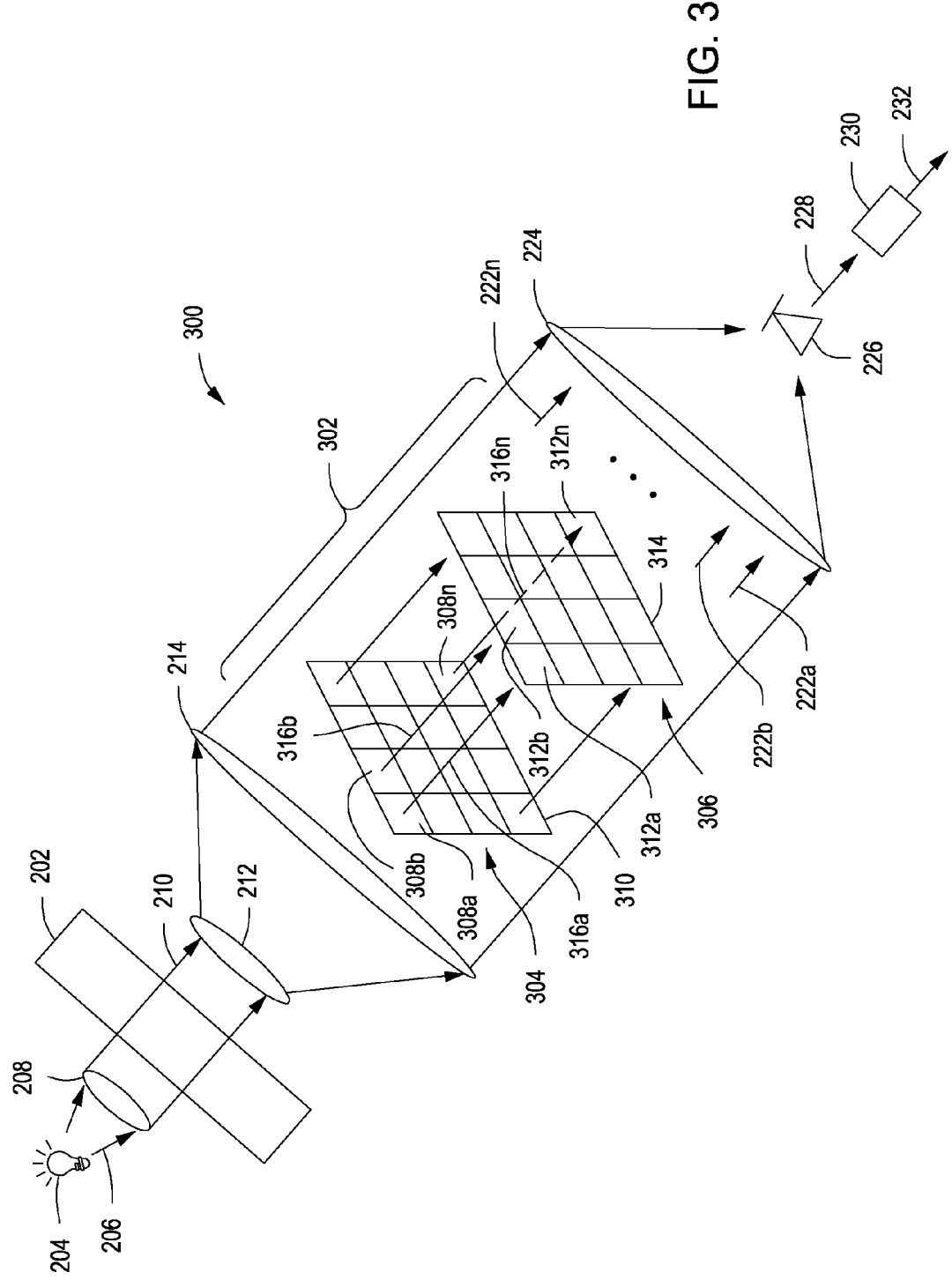
FIG. 3 illustrates another exemplary optical computing device for analyzing a substance, according to one or more embodiments.

Referring now to FIG. 3, illustrated is another exemplary optical computing device 300 (hereafter "device 300") that may be used in analyzing the substance 202, according to one or more embodiments. The device 300 may be similar in some respects to the device 200 of FIG. 2, and therefore may be best understood with reference thereto where like numerals represent like components not described again. As with the device 200 of FIG. 2, the device 300 may be configured to determine a characteristic of interest in the substance 202, such as the concentration of one or more analytes present therein. Unlike the device 200, however, where the processor array 216 (FIG. 2) was able to only detect a single characteristic or analyte, the device 300 may be configured to detect and otherwise analyze multiple characteristics or analytes.

To accomplish this, the device 300 includes a filter array 302 that encompasses an integrated computational element array 304 (hereafter "ICE array 304") and a weighting array 306 arranged adjacent one another in the optical train. The ICE array 304 may include several ICE cores 308 (shown as ICE cores 308a, 308b, . . . and 308n) strategically and individually arranged on a substrate 310. Similar to the ICE cores 218a-n of FIG. 2, each ICE core 308a-n in FIG. 3 may be an optical interference device similar to the ICE core 100 described above with reference to FIG. 1. In other embodiments, however, the ICE cores 308a-n may be any other type of optical device, such as FSS ICE cores, without departing from the scope of the disclosure. The substrate 310 upon which the ICE cores 308a-n are arranged may be similar to the substrate 220 (FIG. 2), and therefore will not be described again.

Similar to the processor array 216 of FIG. 2, the ICE cores 308a-n in the ICE array 304 are separately arranged on the substrate 310 in a square four row by four column matrix, but may equally be arranged in any predetermined pattern or sequence, without departing from the scope of the disclosure. Moreover, the ICE array 304 and its associated substrate 310 need not be square, but could equally be formed in any polygonal shape (e.g., rectangular, hexagonal, pentagonal, etc.), or may be circular, oval, or ovoid in shape, without departing from the scope of the disclosure. Furthermore, while a certain number of ICE cores 308a-n is depicted in FIG. 3 as being arranged on the substrate 310, those skilled in the art will again recognize that more or less ICE cores 308a-n than the number of those depicted may be employed in the device 300.

Each ICE core 308a-n arranged on the substrate 310 may be configured to detect a particular characteristic of the substance 202. In some embodiments, two or more of the ICE cores 308a-n may be configured to detect the same characteristic of interest. In other embodiments, however, each ICE core 308a-n may be configured to detect a different or distinct characteristic of interest of the substance 202.

The weighting array 306 may include a plurality of weighting devices 312 (depicted as weighting devices 312a, 312b, . . . 312n) strategically arranged on a weighting substrate 314. Similar to the substrate 310, the weighting substrate 314 may be similar to the substrate 220 (FIG. 2), and therefore will not be described again. The weighting devices 312a-n may be individually and separately arranged on the weighting substrate 314 such that each axially and optically aligns with a corresponding one of the ICE cores 308a-n. Accordingly, in the illustrated embodiment, the weighting devices 312a-n are arranged on the weighting substrate 314 in a four-by-four square matrix, such that the first weighting device 312a is optically aligned with the first ICE core 308a, the second weighting device 312b is optically aligned with the second ICE core 308b, and so on until the $n^{th}$ weighting device 312n is optically aligned with the $n^{th}$ ICE core 308n.

As a result, the number of ICE cores 308a-n may generally be the same as the number of weighting devices 312a-n. Moreover, any changes to the structural configuration of the ICE array 304 may be substantially mimicked by the weighting array 306 such that axially adjacent ICE cores 308a-n and weighting devices 312a-n remain "optically coupled," meaning that they remain axially and optically aligned within the optical train while the substance 202 is being analyzed.

While depicted in FIG. 3 as being axially offset from each other by a short distance, the ICE array 304 and the weighting array 306 may be arranged at any offset distance from each other. As will be appreciated by those skilled in the art, however, it may prove advantageous to arrange the ICE array 304 and the weighting array 306 fairly close to each other and otherwise substantially adjacent one another. Doing so may have the effect of avoiding or otherwise mitigating cross talk of ICE cores 308a-n with the wrong (not axially adjacent) weighting devices 312a-n. Accordingly, the exploded view of the ICE array 304 and the weighting array 306 is depicted merely for illustrative purposes and therefore is not to be considered as limiting the scope of the disclosure.

Each weighting device 312a-n acts as a broadband neutral density filter that has a particular and predetermined weighting factor associated therewith. For instance, in at least one embodiment, the weighting devices 312a-n may each be a neutral density filter that exhibits a particular weighting factor configured to reduce the normalized intensity of the optical responses of each ICE core 308a-n ranging from 0 to 1, where 0 is a minimum intensity of light transmitted, and 1 is the maximum intensity of light transmitted. As a result, the intensity of the optical response from each ICE core 308a-n may be reduced and otherwise affected by the corresponding weighting device 312a-n, thereby resulting in a weighted output that is directed more to the characteristic of interest.

In operation, the ICE cores 308a-n each receive and optically interact with the sample interacted radiation 210, and thereby produce corresponding optical responses 316 (shown as optical responses 316a, 316b, and 316n). Each optical response 316a-n may be received by a corresponding one of the weighting devices 312a-n arranged on the weighting array 306. More particularly, the first optical response 316a may be received by the first weighting device 312a, the second optical response 316b may be received by the second weighting device 312b, and the $n^{th}$ optical response 316n may be received by the $n^{th}$ weighting device 312n. Each weighting device 312a-n optically interacts with the optical responses 316a-n and generates the corresponding beams of modified electromagnetic radiation 222a-n.

Similar to the device 200 of FIG. 2, the modified electromagnetic radiation 222a-n may then be conveyed to the detector 226 and the signal processor 230 for processing, thereby generating the resulting output signal 232 corresponding to the characteristic of interest of the substance 202. Moreover, since the weighting factors are applied optically to the optical responses 316a-n for each ICE core 308a-n prior to reaching the detector 226, the signal processor 230 is again not required to subsequently apply the weighting factors during computation. Rather, mathematically, the detector 226 sees the weighted modified electromagnetic radiation 222a-n responses simultaneously, and not in time, whereby only one optical measurement needs to be made since the measurements are being made in parallel and not sequentially.

Unlike the device 200 of FIG. 2, however, the filter array 302 is a dynamic component of the device 300. More particularly, the weighting array 306 may be movable and otherwise dynamically changeable in order to vary the weighting factors of each weighting device 312a-n in real-time for the given ICE array 304. As a result, and with reference again to Equations (1) and (2) above, the weighting factors $W_i$ for the optical transmission functions $A_i(\lambda)$ of each ICE core 308a-n may be varied, thereby resulting in a new filter function $F_i(\lambda)$ for each dynamic change applied to the weighting array 306. As will be appreciated, dynamically varying the weighting array 306 may allow the device 300 to detect several characteristics of interest or analytes with a single ICE array 304. For instance, with a particular weighting array 306 having weighting devices 312a-n that each exhibit a particular weighting factor, the ICE array 304 may be configured to detect the concentration of a first analyte. However, with a second weighting array 306 having weighting devices 312a-n that each exhibit a second weighting factor different than the first weight factor, the ICE array 304 may be configured to detect the concentration of a second analyte. Accordingly, the weighting factors may be dynamically changed in the weighting array 306 in order to detect or otherwise analyze any number of characteristics of the substance 202.

In some embodiments, the weighting devices 312a-n for the weighting array 306 may be or otherwise incorporate the use of adjustable optical irises having a mechanical aperture. In operation, each optical iris may be movable or changeable in real-time by an operator, thereby altering the diameter of each corresponding mechanical aperture. Each optical iris, for example, may be operatively coupled to an actuation device or the like, where the actuation device is configured to manipulate the size of the mechanical aperture. As can be appreciated, changing the size of the mechanical apertures may result in a corresponding change to the intensity of light that is able to pass through each weighting device 312a-n, and thereby controlling the intensity of the modified electromagnetic radiation 222a-n. As a result, a different characteristic of interest of the substance 202 may be detectable using the device 300.

In other embodiments, the weighting array 306 may be arranged on a movable assembly (not shown). The movable assembly may be a wheel configured to rotate about a central axis and the weighting devices 312a-n may be neutral density filters, pinholes or apertures of a certain size, exhibiting corresponding predetermined weighting factors. As the movable assembly rotates, the weighting devices 312a-n are able to be optically coupled with different ICE cores 308a-n, and thereby optically interact with different optical responses 316a-n. In at least one embodiment, the movable assembly may incrementally move the weighting array 306 such that individual weighting devices 312a-n are able to optically interact with more than one optical response 316a-n depending on the angular rotation of the movable assembly. As a result, several different characteristics of interest of the substance 202 may be detectable as the movable assembly rotates.

In other embodiments, the weighting array 306 may be a first weighting array arranged on the movable assembly (not shown), and the movable assembly may include at least a second or additional weighting array (not shown). The movable assembly may be configured to selectively move the first and second weighting arrays into the optical train such that each weighting array may apply a different set of weighting factors to the optical responses 316a-n of the ICE cores 308a-n. As a result, the intensity of each optical response 316a-n may be selectively manipulated and otherwise altered, thereby allowing the device 300 to detect an additional or different characteristic of interest of the substance 202.

In such embodiments, the weighting devices 312a-n of each weighting array (e.g., the first and second weighting arrays) may be neutral density filters exhibiting corresponding predetermined weighting factors. Likewise, in such embodiments, the weighting devices 312a-n of each weighting array may be corresponding pinholes or apertures of a certain size exhibiting corresponding predetermined weighting factors.

In embodiments where the movable assembly is a rotatable wheel, the movable assembly may be moved such that the various weighting arrays (e.g., the first and second weighting arrays) are able to optically interact with the optical responses 316a-n of the ICE cores 308a-n at preselected intervals. In other embodiments, the movable assembly may be a linear array or structure having the various weighting arrays (e.g., the first and second weighting arrays) strategically arranged thereon. As the linear structure oscillates in a linear path, the various weighting arrays associated therewith are able to optically interact with the optical responses 316a-n of the ICE cores 308a-n at preselected intervals.

In other embodiments, the weighting array 306 may be generally static within the optical train, but the weighting devices 312a-n associated therewith may be tunable filters and otherwise changeable in real-time by the operator. For instance, in at least one embodiment, the weighting devices 312a-n may be microelectromechanical systems (MEMS) mirrors. In other embodiments, the tunable filters may be other opto-electric filters such as, but not limited to, tunable Fabry-Perot etalons or cavities, acoustic tunable optical filters, or lithium niobate modulators. In yet other embodiments, the weighting devices 312a-n may be liquid crystal tunable filters, without departing from the scope of the disclosure. In such embodiments, the tunable weighting devices 312a-n may be selectively tuned or altered by the operator such that a predetermined weighting factor is applied at each weighting device 312a-n, and thereby controlling the intensity of the modified electromagnetic radiation 222a-n received by the detector 226.

In some embodiments, the weighting array 306 may further include an array of polarizing filters (not shown) coupled to each weighting device 312a-n or otherwise forming an integral part thereof. The polarization of the individual weighting devices 312a-n may have varying orientations. As a result, if a linear polarizer (not shown) is rotated either in front of or behind the weighting array 306 within the optical train, the intensity of the modified electromagnetic radiation 222a-n received by the detector 226 through each weighting device 312a-n will depend on the relative angular displacement of the weighting array 306 and the linear polarizer. Moreover, as will be appreciated, two polarizing films may act like a neutral density filter whose transmittance intensity changes with respect to angle. In addition, FSS based filters can be made with polarization dependent spectra. For example, an FSS ICE core can be constructed in order to be responsive to various analytes depending on the state of polarization of the incident light.

While the dynamic weighting array(s) 306 described and illustrated herein are depicted as being optically coupled to the ICE array 304, it will be appreciated that the dynamic weighting array 306 may be arranged at any location along the optical path between the light source 204 and the detector 226 and obtain equally the same results. In some embodiments, for example, the weighting array 306 may be placed between the light source 204 and the substance 202. In other embodiments, the weighting array 306 may be placed between the substance 202 and the ICE array 304. Those skilled in the art will readily recognize the several different configurations and arrangements of the dynamic weighting array 306 within device 300, without departing from the scope of the disclosure.

In further embodiments, the weighting array 306 may be a first weighting array and the device 300 may include one or more additional weighting arrays (not shown). The additional weighting arrays may be arranged at any location along the optical train (i.e., between the light source 204 and the detector 226) in order to further manipulate the intensity of the modified electromagnetic radiation 222a-n received by the detector 226.

Figure 4A:
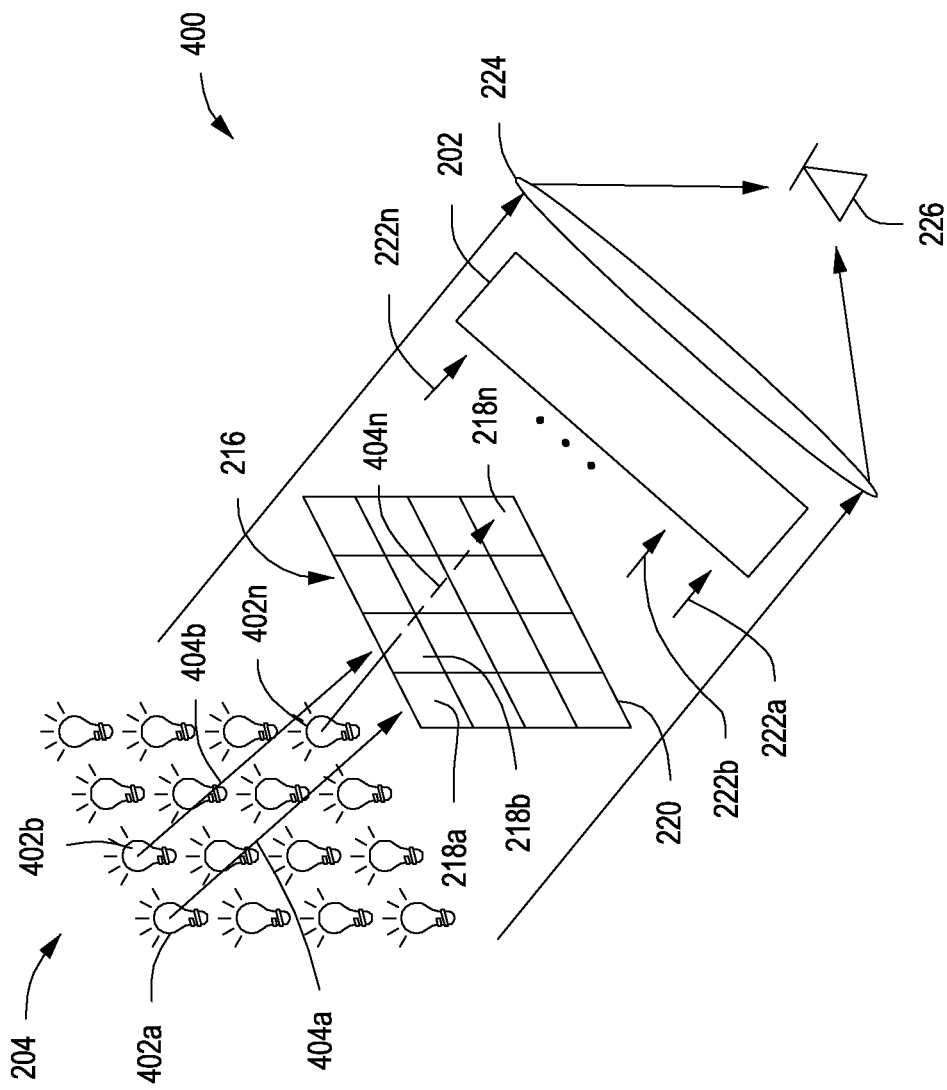
FIG. 4A illustrates another exemplary optical computing device for analyzing a substance, according to one or more embodiments.

Referring now to FIGS. 4A-4F, illustrated are variations and alternative embodiments for the various optical computing devices described herein. Like numerals used in prior figures represent like components that will not be described again. Referring particularly to FIG. 4A, illustrated is another exemplary optical computing device 400 (hereafter "device 400") that may be used in analyzing the substance 202, according to one or more embodiments. The device 400 may include the processor array 216 of FIG. 2, where the ICE cores 218a-n are individually arranged on the substrate 220.

The ICE cores 218a-n in the processor array 216 of FIG. 4A, however, do not have a weighting factor integrally formed therewith, as generally described above. Rather, the light source 204 may provide varying weighting factors for the ICE cores 218a-n. More particularly, the light source 204 may include several individual light source elements 402 (shown as light source elements 402a, 402b, . . . and 402n) configured to emit corresponding beams of electromagnetic radiation 404 (shown as electromagnetic radiation 404a, 404b, and 404n). Each light source element 402a-n may be optically coupled to a corresponding ICE core 218a-n. Accordingly, the first light source element 402a may be configured to provide electromagnetic radiation 404a to the first ICE core 218a, the second light source element 402b may be configured to provide electromagnetic radiation 404b to the second ICE core 218b, and the $n^{th}$ light source element 402n may be configured to provide electromagnetic radiation 404n to the $n^{th}$ ICE core 218n.

While depicted in FIG. 4A as being axially offset from each other by a short distance, the light source 204 and the processor array 216 may be arranged at any offset distance from each other. As will be appreciated by those skilled in the art, however, it may prove advantageous to arrange the light source 204 and the processor array 216 fairly close to each other and otherwise substantially adjacent one another. Doing so may avoid or otherwise mitigate cross talk of light source elements 402a-n with the wrong (not axially adjacent) ICE cores 218a-n. Accordingly, the exploded view of FIG. 4A is depicted merely for illustrative purposes and therefore is not to be considered as limiting the scope of the disclosure.

In operation, the intensity of each light source element 402a-n may be dynamically adjusted or otherwise manipulated in real-time by an operator in order to alter the corresponding weighting factors for each ICE core 218a-n. As a result, the operator may be able to selectively tune each light source element 402a-n such that a predetermined weighting factor is applied at each ICE core 218a-n, and thereby control the intensity of the modified electromagnetic radiation 222a-n that is subsequently received by the detector 226.

Figure 4B:
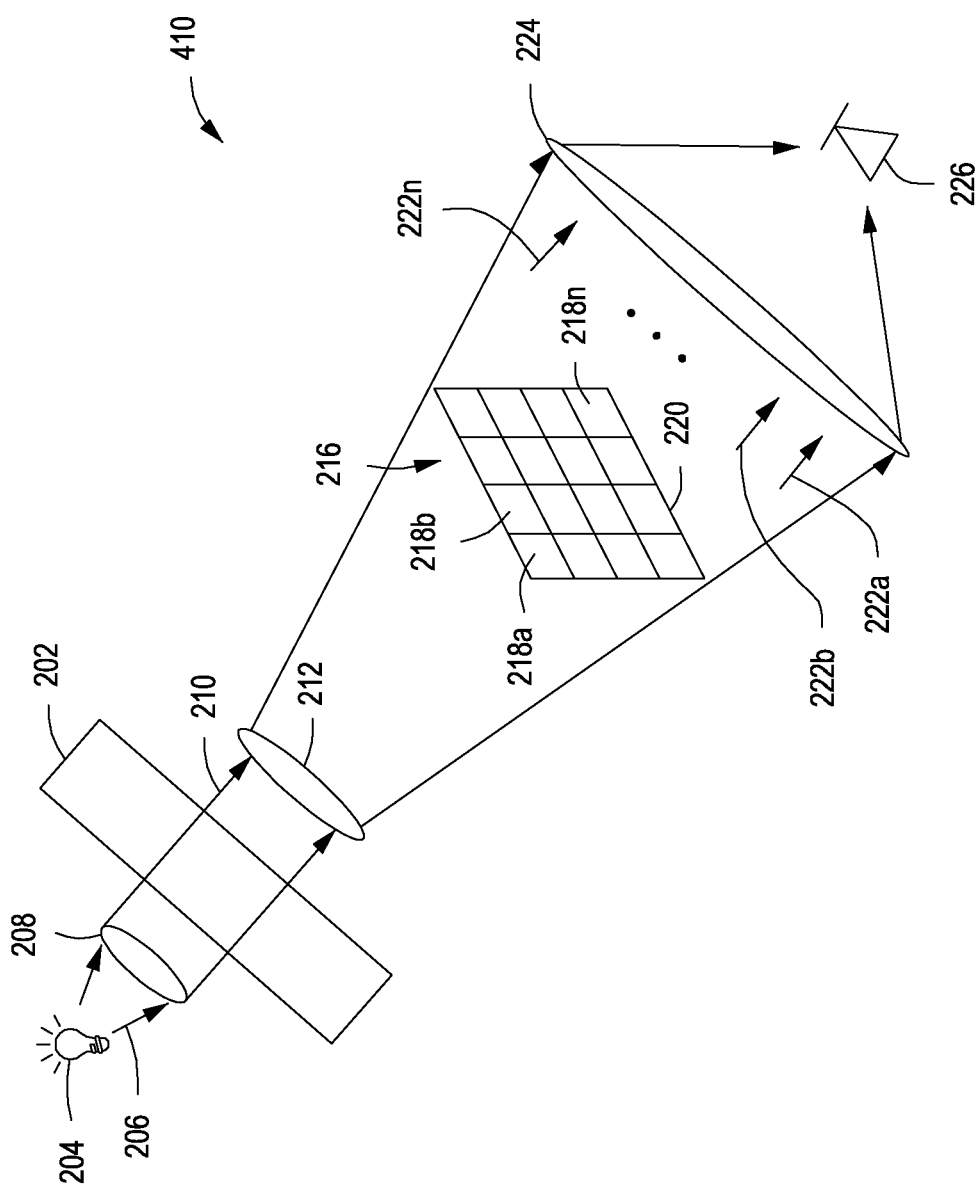
FIG. 4B illustrates another exemplary optical computing device for analyzing a substance, according to one or more embodiments.

Referring to FIG. 4B, illustrated is another exemplary optical computing device 410 (hereafter "device 410") that may be used in analyzing the substance 202, according to one or more embodiments. The device 410 may include the processor array 216 of FIG. 2, where the ICE cores 218a-n are individually arranged on the substrate 220 and corresponding weighting factors are applied thereto and otherwise form an integral part of each ICE core 218a-n.

Unlike the device 200 of FIG. 2, however, the second collimator 214 (FIG. 2) may be omitted from the optical train. Instead, the electromagnetic radiation 206 may be expanded via the expander 212 until it impinges on the optical focusing element 224. Optical interaction of the electromagnetic radiation 206 with the processor array 216 may be accomplished as described above with reference to FIG. 2, thereby resulting in the various beams of modified electromagnetic radiation 222a-n being received by the detector 226.

Figure 4C:
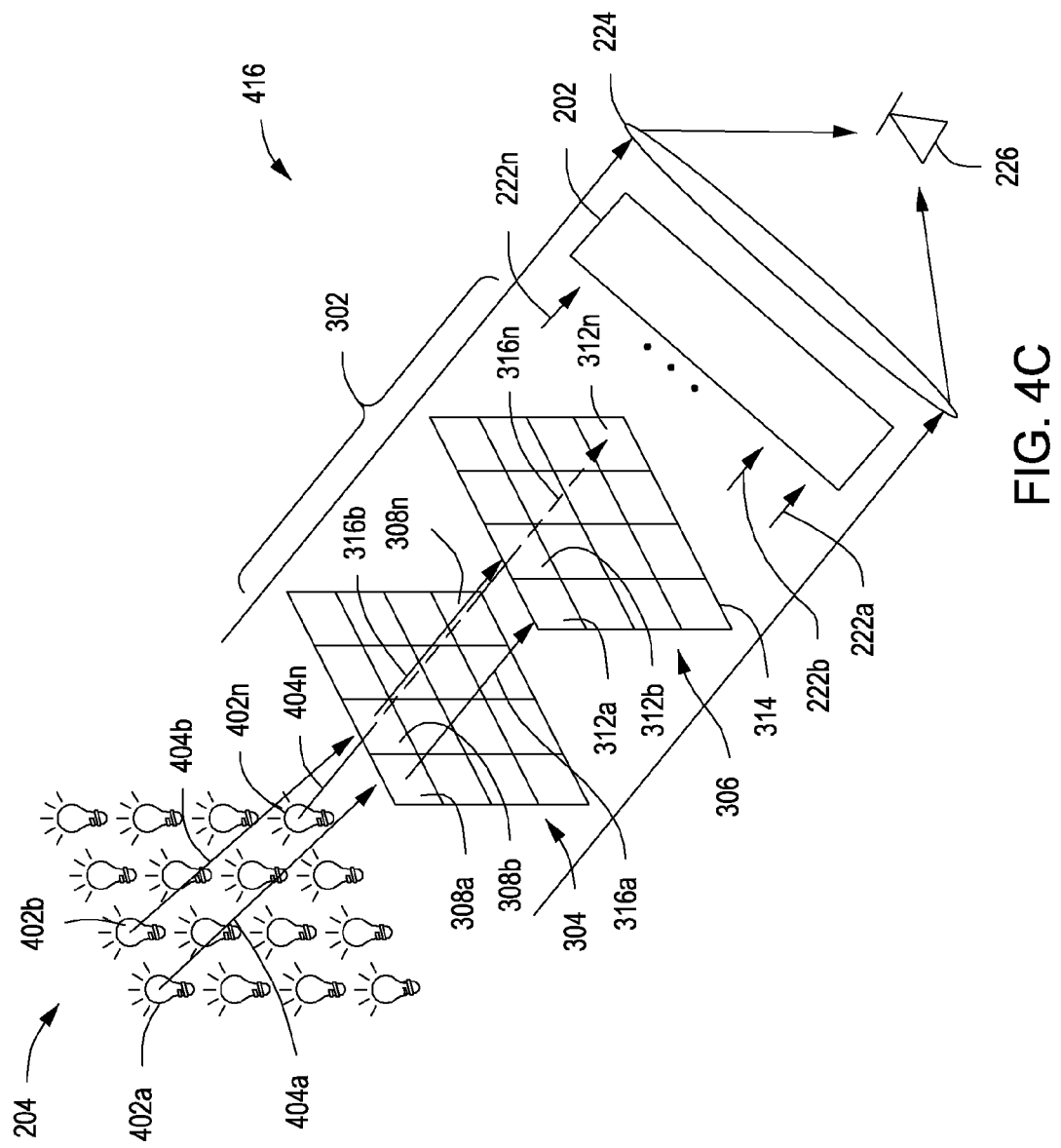
FIG. 4C illustrates another exemplary optical computing device for analyzing a substance, according to one or more embodiments.

Referring to FIG. 4C, illustrated is another exemplary optical computing device 416 (hereafter "device 416") that may be used in analyzing the substance 202, according to one or more embodiments. The device 416 may include the filter array 302 of FIG. 3, which encompasses the ICE array 304 and the dynamic weighting array 306, as generally described above. Moreover, similar to the device 400 of FIG. 4A, the light source 204 may include the several individual light source elements 402a-n that emit corresponding beams of electromagnetic radiation 404a-n configured to optically interact with axially adjacent corresponding ICE cores 308a-n.

More particularly, in the illustrated embodiment, each light source element 402a-n may be optically coupled to a corresponding ICE core 308a-n of the ICE array 304. Accordingly, the first light source element 402a may be configured to provide electromagnetic radiation 404a to the first ICE core 308a, the second light source element 402b may be configured to provide electromagnetic radiation 404b to the second ICE core 308b, and the $n^{th}$ light source element 402n may be configured to provide electromagnetic radiation 404n to the $n^{th}$ ICE core 308n. However, as discussed above, it will be appreciated that the weighting array 306 may be arranged prior to the ICE array 304 within the optical train, such as interposing the light source 204 and the ICE array 304, without departing from the scope of the disclosure.

In operation, each light source element 402a-n may work in conjunction with the weighting array 306 such that the various weighted beams of modified electromagnetic radiation 222a-n are eventually generated and provided to the detector 226 for quantification. In some embodiments, for example, one or more of the light source elements 402a-n may be configured to apply a predetermined weighting factor to its corresponding beam of electromagnetic radiation 404a-n. In other embodiments, no determinable weighting factors are applied through the light source elements 402a-n. Rather, the weighting factors may be principally applied via the weighting array 306, as generally described above with reference to FIG. 3.

Figure 4D:
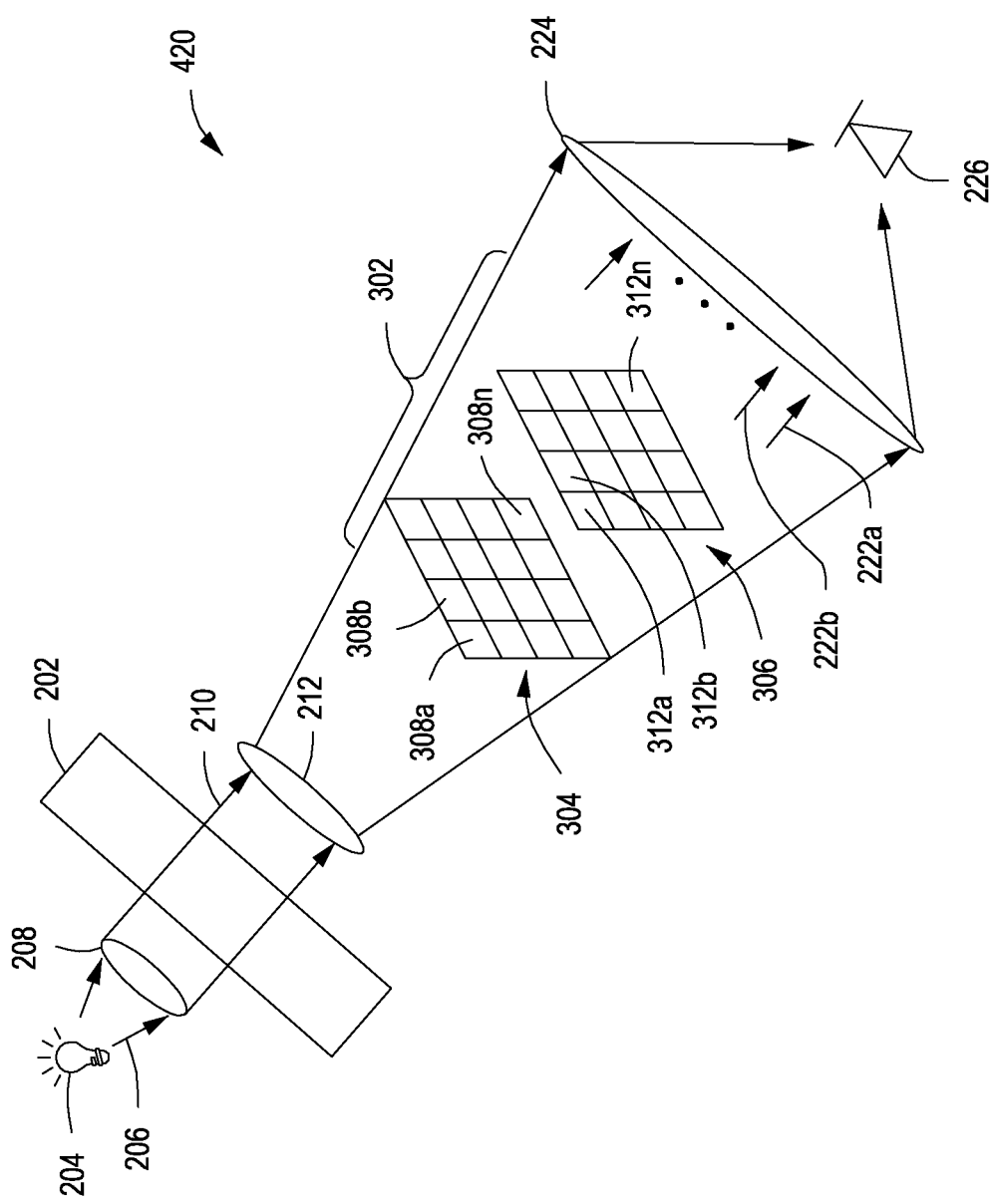
FIG. 4D illustrates another exemplary optical computing device for analyzing a substance, according to one or more embodiments.

Referring to FIG. 4D, illustrated is another exemplary optical computing device 420 (hereafter "device 420") that may be used in analyzing the substance 202, according to one or more embodiments. The device 420 may include the filter array 302 of FIG. 3, and thereby encompasses the ICE array 304 and the dynamic weighting array 306, as generally described above. Moreover, similar to the device 410 of FIG. 4B, the second collimator 214 (FIG. 2) may be omitted from the optical train in the device 420. Instead, the electromagnetic radiation 206 may be expanded via the expander 212 until eventually impinging on the optical focusing element 224. Optical interaction of the electromagnetic radiation 206 with the filter array 302 may be accomplished as described above with reference to FIG. 3, thereby resulting in the various beams of modified electromagnetic radiation 222a-n that are subsequently received by the detector 226.

Figure 4E:
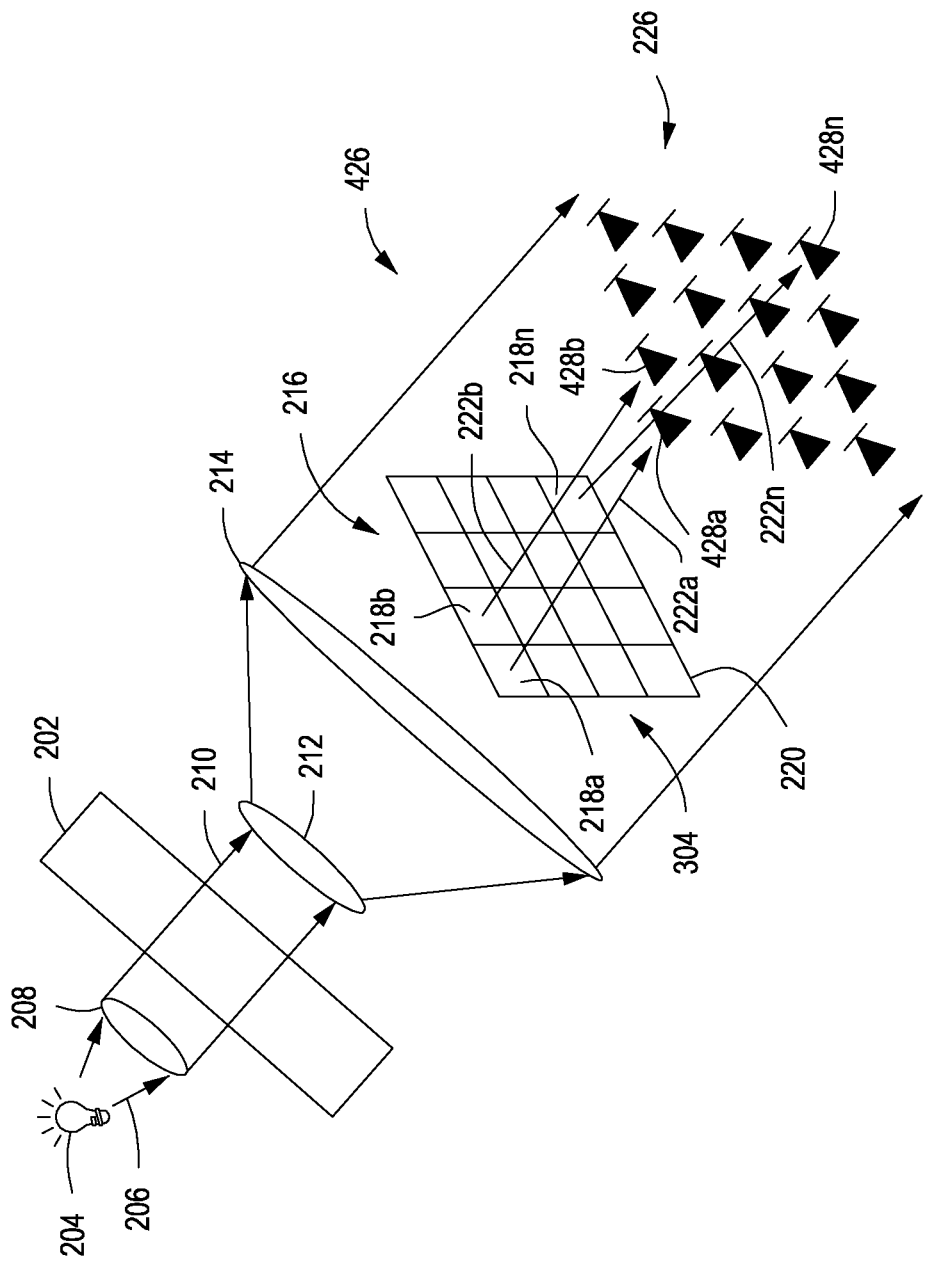
FIG. 4E illustrates another exemplary optical computing device for analyzing a substance, according to one or more embodiments.

Referring to FIG. 4E, illustrated is another exemplary optical computing device 426 (hereafter "device 426") that may be used in analyzing the substance 202, according to one or more embodiments. The device 426 may include the processor array 216 of FIG. 2, where the ICE cores 218a-n are individually arranged on the substrate 220. The ICE cores 218a-n in the processor array 216 of FIG. 4E, however, do not have a weighting factor integrally formed therewith, as generally described above.

As illustrated, the detector 226 in the device 426 may include a plurality of detectors 428 (shown as detectors 428a, 428b, . . . and 428n) arranged to receive the corresponding beams of modified electromagnetic radiation 222a-n generated by the processor array 216. More particularly, in the illustrated embodiment, each detector 428a-n may be optically coupled to a corresponding beam of modified electromagnetic radiation 222a-n. Accordingly, the first detector 428a may be configured to receive the first beam of modified electromagnetic radiation 222a, the second detector 428b may be configured to receive the second beam of modified electromagnetic radiation 222b, and the $n^{th}$ detector 428n may be configured to receive the $n^{th}$ beam of modified electromagnetic radiation 222n.

In exemplary operation, each detector 428a-n may be configured to digitally apply a corresponding weighting factor to its corresponding beam of modified electromagnetic radiation 222a-n. The resulting output signals generated by each detector 428a-n may then be computationally combined such that a weighted average is determined, and the weighted average may be indicative of the characteristic of interest of the substance 202 being analyzed.

Figure 4F:
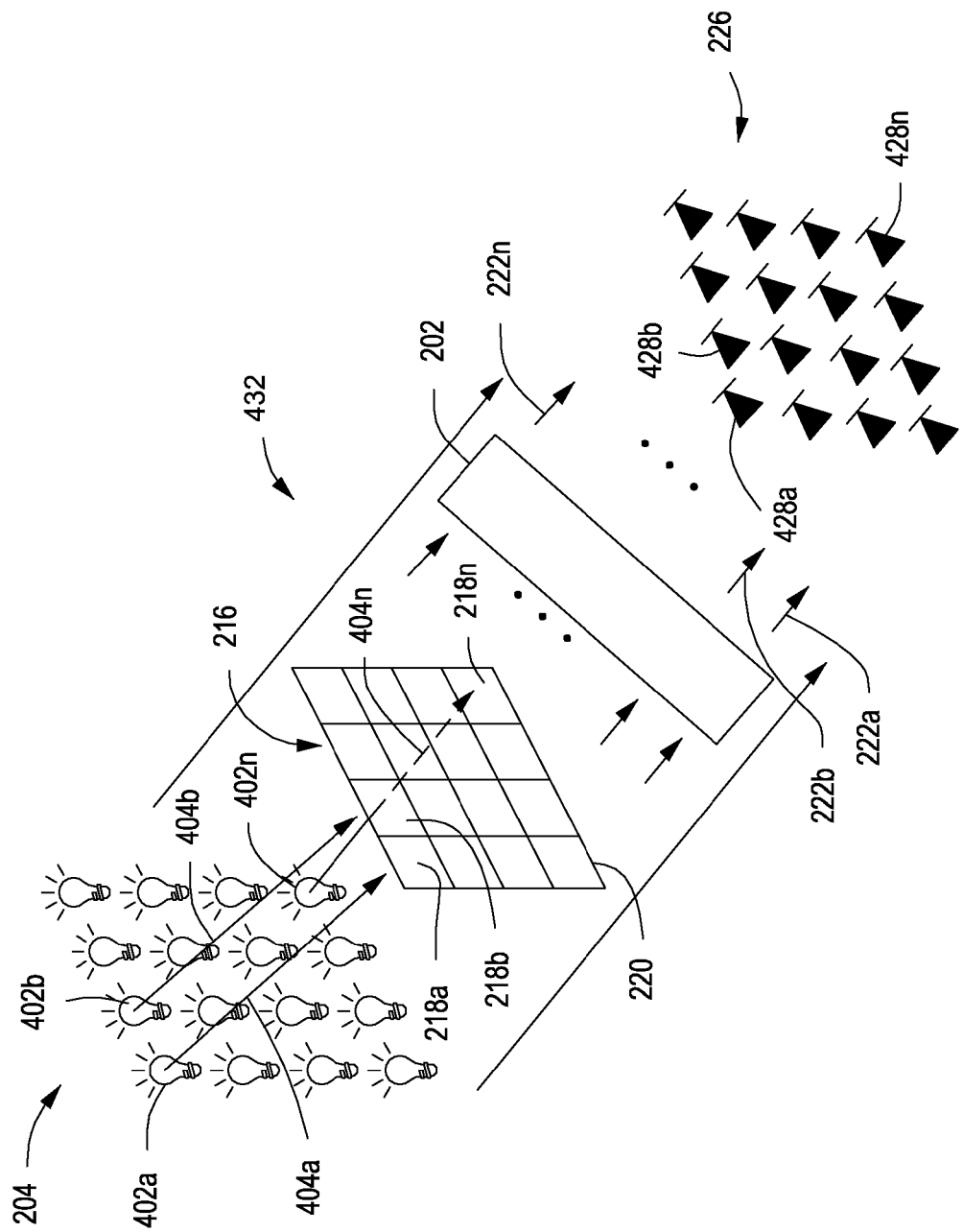
FIG. 4F illustrates another exemplary optical computing device for analyzing a substance, according to one or more embodiments.

Referring to FIG. 4F, illustrated is another exemplary optical computing device 432 (hereafter "device 432") that may be used in analyzing the substance 202, according to one or more embodiments. Similar to the device 400 of FIG. 4A, the device 432 may include the processor array 216 of FIG. 2, where the ICE cores 218a-n are individually arranged on the substrate 220 and do not have a weighting factor integrally formed therewith. Rather, the light source 204 includes the several individual light source elements 402a-n configured to emit corresponding beams of electromagnetic radiation 404a-n. As a result, the first light source element 402a may be configured to provide electromagnetic radiation 404a to the first ICE core 218a, the second light source element 402b may be configured to provide electromagnetic radiation 404b to the second ICE core 218b, and the n$^{th}$ light source element 402n may be configured to provide electromagnetic radiation 404n to the n$^{th}$ ICE core 218n. Moreover, similar to the device 432 of FIG. 4F, the detector 226 in the device 426 includes the plurality of detectors 428a-n arranged to receive the corresponding beams of modified electromagnetic radiation 222a-n.

In exemplary operation, optical interaction of the electromagnetic radiation 404a-n with the corresponding ICE cores 218a-n and the substance 202 results in the generation of the corresponding beams of modified electromagnetic radiation 222a-n to be received by the optically coupled detectors 428a-n. In some embodiments, weighting factors for each ICE core 218a-n may be applied to the modified electromagnetic radiation 222a-n by dynamically adjusting the intensity of each light source element 402a-n. As a result, the operator may be able to selectively tune each light source element 402a-n such that a predetermined weighting factor is applied at each ICE core 218a-n, and thereby control the intensity of the modified electromagnetic radiation 222a-n that is subsequently received by the detector 226.

In other embodiments, weighting factors for each ICE core 218a-n may be applied to the modified electromagnetic radiation 222a-n digitally in each corresponding detector 428a-n. The resulting output signals generated by each detector 428a-n may then be computationally combined such that a weighted average is determined, and the weighted average may be indicative of the characteristic of interest of the substance 202 being analyzed.

In yet other embodiments, a combination of dynamically adjusting the intensity of each light source element 402a-n and digitally applying the weighting factors in the detectors 428a-n may be employed to properly apply weighting factors for each ICE core 218a-n to the modified electromagnetic radiation 222a-n. Those skilled in the art will readily appreciate the various alternative configurations that the device 432 may assume, without departing from the scope of the disclosure. For instance, in at least one embodiment, the processor array 216 may alternatively interpose the substance 202 and the detectors 428a-n.

As used herein, the term "flow path" refers to a route through which a fluid is capable of being transported between at least two points. In some cases, the flow path need not be continuous or otherwise contiguous between the two points. Exemplary flow paths include, but are not limited to, a flow line, a pipeline, production tubing, drill string, work string, casing, a wellbore, an annulus defined between a wellbore and any tubular arranged within the wellbore, a mud pit, a subterranean formation, etc., combinations thereof, or the like. It should be noted that the term "flow path" does not necessarily imply that a fluid is flowing therein, rather that a fluid is capable of being transported or otherwise flowable therethrough.

Embodiments disclosed herein include:

A. An optical computing device that includes a light source that emits electromagnetic radiation into an optical train that extends from the light source to a detector, a substance arranged in the optical train and configured to optically interact with the electromagnetic radiation and produce sample interacted radiation, a processor array arranged in the optical train and including a plurality of integrated computational elements (ICE) arranged on a substrate and configured to optically interact with the electromagnetic radiation, wherein the detector receives a plurality of beams of modified electromagnetic radiation generated through optical interaction of the electromagnetic radiation with the substance and the processor array, and a weighting device coupled to one or more of the plurality of ICE to optically apply a weighting factor to the plurality of beams of modified electromagnetic radiation prior to being received by the detector, wherein the detector generates an output signal indicative of a characteristic of the substance based on the plurality of beams of modified electromagnetic radiation.

B. A method that includes generating electromagnetic radiation with a light source, the electromagnetic radiation being emitted into an optical train that extends from the light source to a detector, optically interacting a substance arranged in the optical train with the electromagnetic radiation, optically interacting a processor array arranged in the optical train with the electromagnetic radiation, the processor array including a plurality of integrated computational elements (ICE) arranged on a substrate, generating a plurality of beams of modified electromagnetic radiation through optical interaction of the electromagnetic radiation with the substance and the processor array, optically applying a corresponding weighting factor to each beam of modified electromagnetic radiation with a weighting device coupled to one or more of the plurality of ICE, wherein the weighting device forms an integral part of the one or more of the plurality of ICE, and receiving the plurality of beams of modified electromagnetic radiation with the detector and generating an output signal indicative of a characteristic of the substance with the detector based on the plurality of beams of modified electromagnetic radiation.

Each of embodiments A and B may have one or more of the following additional elements in any combination: Element 1: further comprising a first collimator arranged between the substance and the light source and configured to receive the electromagnetic radiation and direct a collimated beam of the electromagnetic radiation toward the substance, an expander arranged between the substance and the processor array, a second collimator arranged between the expander and the processor array, and an optical focusing element arranged between the processor array and the detector, the optical focusing element being configured to focus the plurality of beams of modified electromagnetic radiation toward the detector for detection. Element 2: wherein the electromagnetic radiation is at least one of transmitted through and reflected off the substance. Element 3: wherein the sample interacted radiation is generated by an evanescent wave. Element 4: wherein one or more of the plurality of ICE is a frequency selective surface ICE core. Element 5: wherein the weighting device forms an integral part of the one or more of the plurality of ICE. Element 6: wherein the weighting device comprises at least one of a neutral density filter, an optical iris, and a pinhole aperture. Element 7: further comprising a signal processor configured to receive the output signal from the detector and determine the characteristic of the substance, the signal processor including a processor and a machine-readable storage medium having instructions stored thereon, which, when executed by the processor, cause the signal processor to determine the characteristic of the substance. Element 8: wherein the processor array is configured to receive the sample interacted radiation and generate the plurality of beams of modified electromagnetic radiation. Element 9: wherein the light source comprises a plurality of light source elements. Element 10: wherein an expander is arranged between the light source and the substance. Element 11: further comprising a spatial filter arranged in the optical train prior to the processor array.

Element 12: further comprising collimating the electromagnetic radiation with a collimator arranged between the light source and the processor array, and focusing the plurality of beams of modified electromagnetic radiation toward the detector with an optical focusing element arranged between the processor array and the detector. Element 13: wherein optically interacting the substance with the electromagnetic radiation comprises at least one of transmitting the electromagnetic radiation through the substance and reflecting the electromagnetic radiation off the substance. Element 14: wherein the weighting device comprises at least one of a neutral density filter, an optical iris, and a pinhole aperture. Element 15: further comprising receiving the output signal from the detector with a signal processor, the signal processor including a processor and a machine-readable storage medium having instructions stored thereon, which, when executed by the processor, cause the signal processor to determine the characteristic of the substance, and determining the characteristic of the substance with the signal processor. Element 16: further comprising generating sample interacted radiation with the substance upon optically interacting with the electromagnetic radiation, receiving the sample interacted radiation with the processor array, and generating the plurality of beams of modified electromagnetic radiation with the processor array. Element 17: wherein generating the sample interacted radiation with the substance comprises generating the sample interacted radiation from an evanescent wave. Element 18: wherein the light source comprises a plurality of light source elements, and wherein generating electromagnetic radiation with the light source comprises generating a corresponding plurality of beams of electromagnetic radiation with the plurality of light source elements. Element 19: further comprising expanding the electromagnetic radiation with an expander arranged between the light source and the substance. Element 20: further comprising generating a beam of electromagnetic radiation with uniform irradiance across the processor array with a spatial filter arranged in the optical train prior to the processor array.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. An optical computing device, comprising:
a light source that emits electromagnetic radiation into an optical train that extends from the light source to a detector, wherein the electromagnetic radiation optically interacts with a substance arranged in the optical train to produce sample interacted radiation;
a processor array arranged in the optical train and including a plurality of integrated computational elements (ICE) arranged on a common substrate to optically interact with the electromagnetic radiation and generate a corresponding plurality of beams of modified electromagnetic radiation, wherein one or more of the plurality of ICE comprise alternating thin film layers of materials whose index of refraction is high and low, respectively, and wherein the detector receives the plurality of beams of modified electromagnetic radiation; and
a weighting array arranged in the optical train and optically coupled to the processor array, wherein the weighting array includes one or more weighting devices optically aligned with one or more of the plurality of ICE to optically apply a weighting factor to the plurality of beams of modified electromagnetic radiation prior to being received by the detector, and wherein the detector generates an output signal indicative of a characteristic of the substance based on the plurality of beams of modified electromagnetic radiation.

2. The device of claim 1, further comprising:
a first collimator arranged between the substance and the light source and configured to receive the electromagnetic radiation and direct a collimated beam of the electromagnetic radiation toward the substance;
an expander arranged between the substance and the processor array;
a second collimator arranged between the expander and the processor array; and
an optical focusing element arranged between the processor array and the detector, the optical focusing element being configured to focus the plurality of beams of modified electromagnetic radiation toward the detector for detection.

3. The device of claim 2, wherein the electromagnetic radiation is at least one of transmitted through and reflected off the substance.

4. The device of claim 1, wherein the sample interacted radiation is generated by an evanescent wave.

5. The device of claim 1, wherein one or more of the plurality of ICE is a frequency selective surface ICE core.

6. The device of claim 1, wherein one or more of the weighting devices forms an integral part of the one or more of the plurality of ICE.

7. The device of claim 6, wherein one or more of the weighting devices comprises at least one of a neutral density filter, an optical iris, and a pinhole aperture.

8. The device of claim 1, further comprising a signal processor configured to receive the output signal from the detector and determine the characteristic of the substance, the signal processor including a processor and a machine-readable storage medium having instructions stored thereon, which, when executed by the processor, cause the signal processor to determine the characteristic of the substance.

9. The device of claim 1, wherein the processor array is configured to receive the sample interacted radiation and generate the plurality of beams of modified electromagnetic radiation.

10. The device of claim 1, wherein the light source comprises a plurality of light source elements.

11. The device of claim 1, wherein an expander is arranged between the light source and the substance.

12. The device of claim 1, further comprising a spatial filter arranged in the optical train prior to the processor array.

13. A method, comprising:
   generating electromagnetic radiation with a light source, the electromagnetic radiation being emitted into an optical train that extends from the light source to a detector;
   optically interacting a substance arranged in the optical train with the electromagnetic radiation;
   optically interacting a processor array arranged in the optical train with the electromagnetic radiation, the processor array including a plurality of integrated computational elements (ICE) arranged on a common substrate, wherein one or more of the plurality of ICE comprise alternating thin film layers of materials whose index of refraction is high and low, respectively;
   generating a plurality of beams of modified electromagnetic radiation through optical interaction of the electromagnetic radiation with the substance and the processor array, wherein each ICE generates a corresponding one of the beams of modified electromagnetic radiation;
   optically applying a weighting factor to each beam of modified electromagnetic radiation with a weighting array arranged in the optical train and optically coupled to the processor array, wherein the weighting array includes one or more weighting devices optically aligned with one or more of the plurality of ICE; and
   receiving the plurality of beams of modified electromagnetic radiation with the detector and generating an output signal indicative of a characteristic of the substance with the detector based on the plurality of beams of modified electromagnetic radiation.

14. The method of claim 13, further comprising:
   collimating the electromagnetic radiation with a collimator arranged between the light source and the processor array; and
   focusing the plurality of beams of modified electromagnetic radiation toward the detector with an optical focusing element arranged between the processor array and the detector.

15. The method of claim 13, wherein optically interacting the substance with the electromagnetic radiation comprises at least one of transmitting the electromagnetic radiation through the substance and reflecting the electromagnetic radiation off the substance.

16. The method of claim 13, wherein optically applying the corresponding weighting factor to each beam of modified electromagnetic radiation with the weighting array comprises optically applying the corresponding weighting factor to each beam of modified electromagnetic radiation with the one or more weighting devices that comprise at least one of a neutral density filter, an optical iris, and a pinhole aperture.

17. The method of claim 13, further comprising:
   receiving the output signal from the detector with a signal processor, the signal processor including a processor and a machine-readable storage medium having instructions stored thereon, which, when executed by the processor, cause the signal processor to determine the characteristic of the substance; and
   determining the characteristic of the substance with the signal processor.

18. The method of claim 13, further comprising:
   generating sample interacted radiation with the substance upon optically interacting with the electromagnetic radiation;
   receiving the sample interacted radiation with the processor array; and
   generating the plurality of beams of modified electromagnetic radiation with the processor array.

19. The method of claim 18, wherein generating the sample interacted radiation with the substance comprises generating the sample interacted radiation from an evanescent wave.

20. The method of claim 13, wherein the light source comprises a plurality of light source elements, and wherein generating electromagnetic radiation with the light source comprises generating a corresponding plurality of beams of electromagnetic radiation with the plurality of light source elements.

21. The method of claim 13, further comprising expanding the electromagnetic radiation with an expander arranged between the light source and the substance.

22. The method of claim 13, further comprising generating a beam of electromagnetic radiation with uniform irradiance across the processor array with a spatial filter arranged in the optical train prior to the processor array.

* * * * *